United States Patent [19]

Binderup

[11] Patent Number: 4,732,998
[45] Date of Patent: Mar. 22, 1988

[54] BISPHOSPHONIC ACIDS AND ESTERS

[75] Inventor: Ernst T. Binderup, Tåstrup, Denmark

[73] Assignee: Leo Pharmaceutical Products, Ltd., Ballerup, Denmark

[21] Appl. No.: 852,248

[22] PCT Filed: Jul. 25, 1985

[86] PCT No.: PCT/DK85/00071
§ 371 Date: Mar. 31, 1986
§ 102(e) Date: Mar. 31, 1986

[87] PCT Pub. No.: WO86/00902
PCT Pub. Date: Feb. 13, 1986

[30] Foreign Application Priority Data

Jul. 31, 1984 [GB] United Kingdom ............... 8419489

[51] Int. Cl.$^4$ ................ C07F 9/38; C07F 9/40
[52] U.S. Cl. ................ 558/161; 260/502.4 P
[58] Field of Search ............ 558/161; 260/502.4 P

[56] References Cited
FOREIGN PATENT DOCUMENTS
772152 2/1983 U.S.S.R. ............... 260/502.4 P

*Primary Examiner*—Anton H. Sutto
*Attorney, Agent, or Firm*—Cushman, Darby & Cushman

[57] ABSTRACT

The present invention relates to hitherto unknown compounds of the formula I

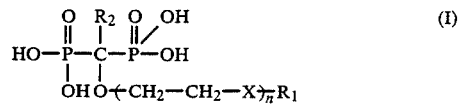

in which $R_1$ is a straight or branched, saturated or unsaturated aliphatic or alicyclic $C_1$-$C_{10}$ hydrocarbon radical, an aryl or an aryl-$C_1$-$C_4$-alkyl radical, $R_1$ if desired being unsubstituted or substituted with straight or branched $C_1$-$C_4$-alkyl, amino, $C_1$-$C_4$-alkamino, di-($C_1$-$C_4$-alkyl)-amino, carboxy, $C_1$-$C_4$-alkoxycarbonyl, hydroxy, $C_1$-$C_4$-alkoxy, phenoxy, mercapto, $C_1$-$C_4$-alkylthio, phenylthio, halogen, trifluoromethyl; $R_2$ stands for hydrogen, $C_1$-$C_8$-alkyl, aryl-$C_1$-$C_4$-alkyl or halogen; X is O or S, and n is an integer from 0 to 2; with the proviso that $R_2$ cannot be hydrogen or methyl if n=O and $R_1$ is methyl.

The compounds of the invention are valuable in the human and veterinary practice.

10 Claims, No Drawings

BISPHOSPHONIC ACIDS AND ESTERS

The present invention relates to hitherto unknown compounds useful in the human and veterinary therapy, to pharmaceutically acceptable salts and easily hydrolyzable esters thereof, to methods for producing said new compounds, to pharmaceutical compositions containing the new compounds, to dosage units of the compositions, and to methods of treating patients using said compositions and dosage units.

The present compounds have the formula I

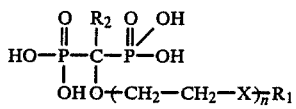

in which $R_1$ is a straight or branched, saturated or unsaturated aliphatic or alicyclic $C_1$–$C_{10}$ hydrocarbon radical, an aryl or an aryl-$C_1$–$C_4$-alkyl radical, $R_1$ if desired being unsubstituted or substituted with straight or branched $C_1$–$C_4$-alkyl, amino, $C_1$–$C_4$-alkylamino, di-($C_1$–$C_4$-alkyl)-amino, carboxy, $C_1$–$C_4$-alkyoxycarbonyl, hydroxy, $C_1$–$C_4$-alkoxy, phenoxy, mercapto, $C_1$–$C_4$-alkylthio, phenylthio, halogen, trifluoromethyl; $R_2$ stands for hydrogen, $C_1$–$C_8$-alkyl, aryl-$C_1$–$C_4$-alkyl or halogen; X is O or S, and n is an integer from 0 to 2; with the proviso that $R_2$ cannot be hydrogen or methyl if n=0 and $R_1$ is methyl.

In particular, $R_1$ stands for straight or branched $C_3$–$C_6$-alkyl, phenyl or benzyl optionally substituted with amino, hydroxy, methyl or halogen, and $R_2$ for hydrogen, straight or branched $C_1$–$C_4$-alkyl, benzyl or halogen; preferably $R_1$ is propyl, butyl, aminopropyl, aminobutyl, 2,2,2-trifluoroethyl, phenyl or tolyl, and $R_2$ is hydrogen, methyl, ethyl or chlorine.

As stated above, the invention also relates to salts of the compounds of formula I which are tetrabasic acids and thus form mono-, di-, tri- and tetrabasic salts with bases. As examples of salts formed with pharmaceutically acceptable, non-toxic bases, mention may be made of alkali metal salts and alkaline earth metal salts, such as lithium, sodium, potassium, magnesium, and calcium salts, as well as salts with ammonia and suitable non-toxic amines, such as lower alkylamines, e.g. triethylamine, lower alkanolamines, e.g. diethanolamine or triethanolamine, procaine, cycloalkylamines, e.g. dicyclohexylamine, benzylamines, e.g. N-methylbenzylamine. N-ethylbenzylamine, N-benzyl-β-phenethylamine, N,N'-dibenzylethylenediamine or dibenzylamine, and heterocyclic amines, e.g. morpholine, N-ethylpiperidine and the like.

Being tetrabasic acids, the compounds of formula I can form mono-, di-, tri- or tetraesters. The esters of the present invention are in vitro easily hydrolyzable esters, the ester forming residue being selected from the group consisting of alkanoyloxymethyl of three to six carbon atoms, 1-(alkanoyloxy)ethyl of four to seven carbon atoms, 1-methyl-1-(alkanoyloxy)ethyl of five to eight carbon atoms, alkoxycarbonyloxymethyl of three to six carbon atoms, 1-(alkoxycarbonyloxy)ethyl of four to seven carbon atoms, 1-methyl-1-(alkoxycarbonyloxy)ethyl of five to eight carbon atoms, 3-phthalidyl, 4-crotonolactonyl, γ-butyrolacton-4-yl, (2-oxo-1,3-dioxolen-4-yl)methyl, (5-methyl-2-oxo-1,3-dioxolen-4-yl)methyl, and (5-phenyl-2-oxo-1,3-dioxolen-4-yl)methyl as well as dialkylaminoalkyl, acetonyl, and methoxymethyl.

Especially preferred are alkanoyloxyalkyl and alkoxycarbonyloxy alkyl esters, such as pivaloyloxymethyl and ethoxycarbonyloxyethyl esters.

The normal bones are living tissues undergoing constant resorption and redeposition of calcium, with the net effect of maintenance of a constant mineral balance. The dual process is commonly called "bone turnover". In normal growing bones, the mineral deposition exceeds the mineral resorption, whereas in certain pathological conditions, bone resorption exceeds bone deposition resulting in e.g. hypercalcemia, for instance due to malignancy or primary hyperparathyroidism, or in osteoporosis. The calcium deposition may also take place in undesirable amounts and areas leading to other pathological conditions, e.g. osteoarthritis, rheumatoid arthritis, atherosclerosis, and Paget's disease which is characterized by a combination of an abnormal high bone resorption followed by abnormal calcium deposition.

Research within other areas affected by calcium deposition and/or resorption, such as the development of detergents for use in areas with hard water, or of toothpastes which could provide a protection against calcium resorption due to acid dissolution or calcium deposition in the form of dental calculus, has been conducted with compounds forming complexes with calcium. Examples of such complex forming compounds are certain bisphosphonates. It has long been known that such compounds can inhibit not only the crystal growth, but also can delay dissolution of already formed crystals.

In spite of the fact that a great number of bisphosphonic acids are known, only a few have been used clinically. An example is 1-hydroxyethylidene-1,1-bisphosphonic acid (etidronate) which is the only marketed compound of this type. It is not very active and inhibits bone mineralization in doses close to those necessary for the more useful inhibition of bone resorption.

Dichlormethylene-bisphosphonic acid (clodronate) has been shown to inhibit bone resorption without affecting bone mineralization, but has been associated with certain adverse affects.

3-Amino-1-hydroxypropylidene-1,1-disphosphonic acid (APD) is more active on a weight basis than the two aforementioned compounds, but has also undesirable effects.

A common drawback of the three abovementioned compounds is their very poor oral absorbability (about 2–6%).

The ideal compound for the purpose is one which is selective, i.e. a compound which only influences one of the processes in the mineral balance, either the resorption or the deposition depending upon the pathological condition treated, and furthermore the ideal compound should be absorbed to a great extent when given orally and should be devoid of side effects.

It has now surprisingly turned out that the present compounds have these desired characteristics. Compared with the compounds known to have a systemic activity, they show a high degree of selectivity combined with a good oral absorbability and a low toxicity.

The activity in inhibiting bone resorption is determined as follows. Female rats (140–160 g) were placed in metabolic cages and urine was collected for 2 days. The compound to be tested was solubilized in a 2% bicarbonate buffer and administered daily subcutaneously at 16 μmol/kg for 7 days. Urine was collected daily, and the urinary content of hydroxyproline (which is an indication of bone resorption, confer P. H. Reitsma et al, Calcif. Tissue Int. 32, 145-157 (1980)), was determined by the method of Prockop and Udenfriend (Anal. Biochem. 1, 228-239, 1960). Inhibition of bone resorption was expressed as % change in hydroxyproline excretion after 7 days of treatment, each rat serving as its own control.

Results of the testing of four compounds of formula I (n=0) together with 3 reference compounds at a dose of 16 μmol/kg/day to groups of 5 rats are given in Table I.

TABLE I

| Compound | $R_1$ | $R_2$ | Example | % change in hydroxyproline excretion (day +3 to +7) s.c. adm. |
|---|---|---|---|---|
| Etidronate | — | — | reference compound | −10 |
| Clodronate | — | — | reference compound | −27 |
| APD | — | — | reference compound | −43 |
| EB 884 | n-$C_5H_{11}$ | H | 6 | −37 |
| EB 890 | n-$C_3H_7$ | H | 6 | −47 |
| EB 891 | n-$C_4H_9$ | H | 5 | −47 |
| EB 899 | $C_6H_5$ | H | 18 | −43 |

The compounds of the present invention with $R_2$=H may be prepared from a dichloromethyl ether of formula II according to the following reaction scheme Tetraalkyl esters may also be cleaved by an alternative and milder method described in Jour. f. prakt. Chemie 320, 344 (1978). Treatment with bromo-trimethylsilane at room temperature or moderately elevated temperature leads to a tetra-trimethylsilyl ester which is easily cleaved with water to yield the free acid of formula I ($R_2$=H).

The compounds of the invention in which $R_2$ is an alkyl or aralkyl radical may be prepared by alkylation of compounds of formula IV, e.g. by treatment with sodium hydride followed by an alkyl or aralkyl halide. The reaction is performed in a suitable solvent, such as dimethylformamide or tetrahydrofuran. Cleavage of the tetraalkyl esters results in the compounds of the invention with $R_2$=alkyl or aralkyl.

The compounds of the invention in which $R_2$=halogen may be prepared by halogenation of compounds of formula IV, e.g. sodium hypochlorite followed by cleavage of the tetraethyl ester.

The present compounds are as mentioned above intended for use in pharmaceutical compositions which are useful in the treatment of osteoporosis, rheumatoid arthritis and other arthritic disorders, atherosclerosis, hypercalcemia due to malignancies or primary hyperparathyroidism, Paget's disease, and other conditions with an abnormal calcium balance.

The compounds of the invention may also be used in the prevention of dental calculus, e.g. as an ingredient in tooth-paste.

The amount required of a compound of formula (I)

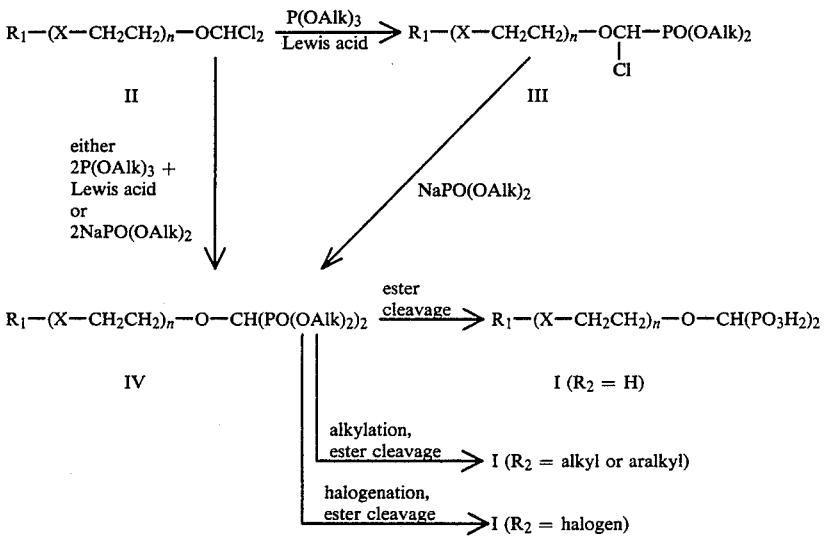

$R_1$, X, and n have the meanings mentioned above and Alk stands for $C_1$-$C_6$-alkyl.

Some of the dichloromethyl ethers of formula II are known. These as well as the unknown can be prepared as described in Chem. Ber. 94, 548 (1961) or in Recueil Des Travaux Chimiques Des Pay-Bas 90, 556 (1971).

As shown in the reaction scheme these dichloromethyl ethers can be converted into tetralkyl esters of formula IV either directly or through intermediates of formula III.

The intermediates of formula III and IV are unknown and are thus part of the invention.

Cleavage of the tetraalkyl esters, e.g. with boiling hydrochloric acid leads to the compounds of the invention with $R_2$=H.

(hereinafter referred to as the active ingredient) for therapeutic effect will, of course, vary both with the particular compound, the route of administration and the mammal under treatment. A suitable dose of a compound of formula (I) for a mammal suffering from e.g. a hypercalcemic condition as defined hereinbefore is 0.01 to 25 mg per kilogram bodyweight, the most preferred dosage being 0.02 to 10 mg/kg of bodyweight, for example 0.05 to 5 mg/kg; administered once or more times daily.

In the case of the prophylactic treatment of e.g. postmenopausal osteoporosis, a suitable daily dose of a compound of formula (I) is 0.01 to 10 mg per kilogram bodyweight, the most preferred dosage being 0.02 to 5 mg/kg of bodyweight.

While it is possible to administer an active compound as such, it is sometimes preferable to present it as a pharmaceutical formulation. Conveniently, the active ingredient comprises from 0.1% to 99.9% by weight of the formulation. Conveniently, dosage units of a formulation contain between 1 mg and 1 g of the active ingredient. For topical administration, the active ingredient preferably comprises from 1% to 2% by weight of the formulation but the active ingredient may comprise as much as 10% w/w.

By the term "dosage unit" is meant a unitary, i.e. a single dose which is capable of being administered to a patient, and which may be readily handled and packed, remaining as a physically stable unit dose comprising either the active material as such or a mixture of it with solid or liquid pharmaceutical diluents or carriers.

The formulations, body for veterinary and for human medical use, of the present invention comprise an active ingredient in association with a pharmaceutically acceptable carrier and optionally other therapeutic ingredient(s). The carrier(s) must be "acceptable" in the sense of being compatible with the other ingredients of the formulations and not deleterious to the recipient thereof.

The formulations include those in a form suitable for oral, rectal, parenteral (including subcutaneous, intramuscular and intravenous), or topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be in the form of a bolus, electuary or paste.

Formulations for rectal administration may be in the form of a suppository incorporating the active ingredient and a carrier such as cocoa butter, or in the form of an enema.

Formulations suitable for parenteral administration conveniently comprise a sterile aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for intra-articular administration.

Formulations suitable for topical administration include liquid or semi-liquid preparations such as liniments, lotions, applications; oil-in-water or water-in-oil emulsions such as creams, ointments or pastes, including tooth-pastes; or solutions or suspensions such as drops.

In addition to the aforementioned ingredients, the formulations of this invention may include one or more additional ingredients such as diluents, buffers, flavouring agents, binders, surface active agents, thickeners, lubricants, preservatives, e.g. methylhydroxybenzoate (including anti-oxidants), emulsifying agents and the like.

The compositions may further contain other therapeutically active compounds usually applied in the treatment of the above mentioned pathological conditions, for instance vitamin $D_2$ and $D_3$ and hydroxylated derivatives, e.g. $1\alpha$-hydroxy-vitamin $D_3$, $1\alpha$-hydroxy-vitamin $D_2$, $1\alpha,25$-dihydroxy-vitamin $D_3$, $1\alpha,25$-dihydroxy-vitamin $D_2$, calcitonin (human, porcine or salmon), mitramycin, sodium fluoride, estrogens, and non-steroid antiinflammatory drugs, e.g. acetylsalicyclic acid, indomethacin, naprosyn, and timegadine.

According to the invention, the present compounds are administered to a patient suffering from one of the above mentioned pathological conditions in a daily dose (for adults) from 0.7 mg to 1750 mg, preferably from 1,5–1000 mg, and in the veterinary practice correspondingly in daily doses from 0.01 to 25 mg/kg bodyweight.

The invention will now be further described in the following non-limiting Examples: (Except where otherwise specified, NMR-spectra have been recorded with tetramethylsilane as internal reference.)

EXAMPLE 1

Diethyl $\alpha$-chloro-$\alpha$-(n-butoxy)-methylphosphonate

A mixture of dichloromethyl butyl ether (13.5 g), triethyl phosphite (16.1 ml) and anhydrous zinc chloride (70 mg) was heated at 100° C. for 1 hour. Distillation in vacuo gave the title compound as a colourless oil.

B.p. 93°–95° C. (0.15 mm Hg).

NMR (CDCl$_3$): $\delta$=0.93 (t, 3H), 1.37 (t, 6H), 1.3–1.8 (m, 4H), 3.4–3.6 (m, 1H), 3.8–4.1 (m, 1H), 4.1–4.5 (m, 4H), and 5.65 (d, 1H) ppm.

EXAMPLE 2

By following the procedure described in Example 1 and by using the appropriate dichloromethyl alkyl ethers the following compounds were prepared:

Diethyl $\alpha$-chloro-$\alpha$-(n-propoxy)-methylphosphonate

B.p. 95°–100° C. (0.75 mm Hg).

NMR (CDCl$_3$): $\delta$=0.96 (t, 3H), 1.37 (t, 6H), 1.65 (m, 2H), 3.4–3.7 (m, 1H), 3.8–4.1 (m, 1H), 4.1–4.5 (m, 4H), and 5.66 (d, 1H) ppm.

Diethyl $\alpha$-chloro-$\alpha$-(n-pentyloxy)-methylphosphonate

B.p. 108°–117° C. (0.1 mm Hg).

NMR (CDCl$_3$): $\delta$=0.90 (t, 3H), 1.37 (t, 6H), 1.3–1.8 (m, 6H), 3.4–3.6 (m, 1H), 3.8–4.1 (m, 1H), 4.2–4.5 (m, 4H), and 5.66 (d, 1H) ppm.

Diethyl $\alpha$-chloro-$\alpha$-(isobutoxy)-methylphosphonate

B.p. 100° C. (0.5 mm Hg).

NMR (CDCl$_3$): $\delta$=0.95 (d, 6H), 1.37 (t, 6H), 1.96 (m, 1H), 3.2–3.4 (m, 1H), 3.7–3.9 (m, 1H), 4.1–4.5 (m, 4H), and 5.65 (d, 1H) ppm.

Diethyl $\alpha$-chloro-$\alpha$-(n-decyloxy)-methylphosphonate

B.p. 171°–175° C. (0.8 mm Hg).

NMR (CDCl$_3$): δ=0.88 (t, 3H), 1.27 (bs, 14H), 1.37 (t, 6H), 1.6 (m, 2H), 3.4–3.7 (m, 1H), 3.8–4.1 (m, 1H), 4.1–4.5 (m, 4H), and 5.65 (d, 1H) ppm.

EXAMPLE 3

Tetraethyl (n-butoxymethylene)-bisphosphonate

Diethyl phosphite (11.6 ml) was added dropwise at 20° C. to a stirred suspension of 55% sodium hydride (3.45 g) in dry tetrahydrofuran (65 ml). After stirring for a further 15 minutes, the mixture was cooled to 0° C., and diethyl α-chloro-α-(n-butoxy)-methylphosphonate (16.5 g) was added during 10 minutes. The mixture was stirred at room temperature for 1 hour, diluted with saturated aqueous sodium chloride and extracted with chloroform. The organic phase was dried and evaporated to leave an oil which was purified by chromatography on silica gel (eluent:ether-acetone 1:1). The pure title compound was isolated as a colourless oil.

NMR (CDCl$_3$): δ=0.92 (t, 3H), 1.35 (t, 12H), 1.2–1.8 (m, 4H), 3.75 (t, 2H), 3.91 (t, 1H), and 4.0–4.4 (m, 8H) ppm.

EXAMPLE 4

By following the procedure described in Example 3 and using the compounds described in Example 2 instead of diethyl α-chloro-α-(n-butoxy)-methylphosphonate, the following compounds were prepared:

Tetraethyl (n-propoxymethylene)-bisphosphonate

NMR (CDCl$_3$): δ=0.94 (t, 3H), 1.36 (t, 12H), 1.65 (m, 2H), 3.72 (t, 2H), 3.92 (t, 1H), and 4.1–4.5 (m, 8H) ppm.

Tetraethyl (n-pentyloxymethylene)-bisphosphonate

NMR (CDCl$_3$): δ=0.89 (t, 3H), 1.35 (t, 12H), 1.2–1.8 (m, 6H), 3.73 (t, 2H), 3.90 (t, 1H), and 4.0–4.4 (m, 8H) ppm.

Tetraethyl (isobutoxymethylene)-bisphosphonate

NMR (CDCl$_3$): δ=0.93 (d, 6H), 1.35 (t, 12H), 1.90 (m, 1H), 3.53 (d, 2H), 3.90 (t, 1H), and 4.0–4.4 (m, 8H) ppm.

Tetraethyl (n-decyloxymethylene)-bisphosphonate

Microanalysis: Calculated: C: 51.34 H: 9.53. Found: C: 51.47 H: 9.64.

EXAMPLE 5

(n-Butoxymethylene)-bisphosphonic acid, tris-benzylamine salt

A mixture of tetraethyl (n-butyoxymethylene)-bisphosphonate (10.0 g) and 6N hydrochloric acid (60 ml) was refluxed overnight. The resulting solution was evaporated to dryness in vacuo. Residual hydrochloric acid was removed by repeated evaporation with abs. ethanol. The crude product was redissolved in abs. ethanol (100 ml), and benzylamine (12.2 ml) was added with stirring. The crystalline salt was isolated by filtration and dried in vacuo.

NMR (CD$_3$OD): δ=0.86 (t, 3H), 1.1–1.8 (m, 4H), 3.70 (t, 1H), 3.80 (t, 2H), 4.04 (s, 6H), and 7.3–7.7 (m, 15H) ppm.

EXAMPLE 6

By following the procedure of Example 5 and using the compounds described in Example 4 instead of tetraethyl (n-butoxymethylene)-bisphosphonate the following compounds were obtained:

(n-Propoxymethylene)-bisphosphonic acid, tris-benzylamine salt

NMR (CD$_3$OD): δ=0.88 (t, 3H), 1.60 (m, 2H), 3.70 (t, 1H), 3.76 (t, 2H), 4.04 (s, 6H), and 7.3–7.7 (m, 15H) ppm.

(n-Pentyloxymethylene)-bisphosphonic acid

This compound was isolated as the free acid in crystalline form.

NMR ((CD$_3$)$_2$SO): δ=0.95 (t, 3H), 1.1–1.8 (m, 6H), 3.70 (t, 2H), and 3.71 (t, 1H) ppm.

The tris-benzylamine salt was also prepared. NMR (D$_2$O): δ=0.70 (t, 3H), 1.0–1.7 (m, 6H), 3.47 (t, 1H), 3.56 (t, 2H), 4.01 (s, 6H), and 7.31 (s, 15H) ppm. HDO=4.66 ppm was used as internal reference.

(Isobutoxymethylene)-bisphosphonic acid, tris-benzylamine salt

NMR (CD$_3$OD): δ=0.90 (d, 6H), 1.88 (m, 1H), 3.59 (d, 2H), 3.71 (t, 1H), 4.04 (s, 6H), and 7.3–7.7 (m, 15H) ppm.

(n-Decyloxymethylene)-bisphosphonic acid, tris-benzylamine salt

NMR (CD$_3$OD): δ=0.87 (t, 3H), 1.23 (s, 14H), 1.4–1.7 (m, 2H), 3.70 (t, 1H), 3.79 (t, 2H), 4.04 (s, 6H), and 7.3–7.6 (m, 15H) ppm.

EXAMPLE 7

By substituting dichloromethyl 3-chloropropyl ether, dichloromethyl 2-ethoxyethyl ether or dichloromethyl 2,2,2-trifluoroethyl ether for dichloromethyl butyl ether in Example 1 and by following the procedures described in Examples 1, 3 and 5 the following compounds are prepared:

(3-chloropropoxymethylene)-bisphosphonic acid, tris-benzyl amine salt

[2-(ethoxy)-ethoxymethylene]-bisphosphonic acid, tris-benzyl amine salt (2,2,2-trifluoroethoxymethylene)-bisphosphonic acid, tris-benzylamine salt. NMR (CD$_3$OD): δ=3.84 (t, J=15 Hz, 1H), 4.04 (s, 6H), 4.31 (q, J=9 Hz, 2H) and 7.4 (m, 15H) ppm.

EXAMPLE 8

Tetraethyl (phenoxymethylene)-bisphosphonate

Diethylphosphite (20.6 ml) was added dropwise at 20° C. to a stirred suspension of 55% sodium hydride (6.24 g) in dimethylformamide (90 ml). After stirring for a further 15 minutes, the mixture was cooled to 0° C., and dichloromethyl phenyl ether (9.27 g) was added dropwise. Stirring was continued overnight at 45° C., and the mixture was cooled in ice, diluted with water, neutralized and extracted with ethyl acetate. The organic phase was washed repeatedly with water, dried and evaporated in vacuo to yield an oil which was purified by chromatography on silica gel. Eluent: ether-acetone 85:15. The pure title compound was obtained as a colourless oil.

NMR (CDCl$_3$): δ=1.22 (t, 6H), 1.25 (t, 6H), 4.1–4.5 (m, 8H), 4.87 (t, 1H), and 6.9–7.5 (m, 5H) ppm.

EXAMPLE 9

Tetraethyl (m-chlorophenoxymethylene)-bisphosphonate

This compound was obtained as described in Example 8 by substituting dichloromethyl m-chlorophenyl ether for dichloromethyl phenyl ether.

NMR (CDCl$_3$): $\delta$=1.25 (t, 6H), 1.27 (t, 6H), 4.1–4.4 (m, 8H), 4.81 (t, 1H) and 6.9–7.3 (m, 4H) ppm.

EXAMPLE 10

(Phenoxymethylene)-bisphosphonic acid, tris-benzylamine salt

This compound was prepared as described in Example 5 by substituting tetraethyl (phenoxymethylene)-bisphosphonate for tetraethyl (n-butoxymethylene)-bisphosphonate. Colourless crystalline salt.

NMR (D$_2$O): $\delta$=4.07 (s, 6H), 4.52 (t, 1H), 6.8–7.4 (m, 5H), and 7.40 (s, 15H) ppm. HDO=4.66 ppm was used as internal reference.

EXAMPLE 11

(m-Chlorophenoxymethylene)-bisphosphonic acid, tris-benzylamine salt

This compound was obtained from tetraethyl (m-chlorophenoxymethylene)-bisphosphonate by following the procedure described in Example 5.

NMR (D$_2$O): $\delta$=4.07 (s, 6H), 4.48 (t, 1H), 6.8–7.3 (m, 4H), and 7.38 (s, 15H) ppm. HDO=4.66 ppm was used as internal reference.

EXAMPLE 12

2-(p-Chlorophenoxy)-ethyl formate p-Chlorophenol (112 g) was added to a solution of sodium hydroxide (40 g) in water (100 ml). The mixture was heated to reflux, and 2-chloroethanol (80 g) was added dropwise with stirring. After cooling to room temperature, the mixture was extracted with ether. The organic phase was dried and evaporated to leave a residue which was refluxed with formic acid (150 ml) for 1 hour followed by distillation in vacuo. The product had boiling point 138°–40° C./1 mm Hg.

EXAMPLE 13

Dichloromethyl 2-(p-chlorophenoxy)-ethyl ether

Phosphorus pentachloride (104 g) was added in portions with stirring at 75° C. to 2-(p-chlorophenoxy)-ethyl formate (94.2 g). The mixture was left overnight at room temperature, and phosphorus oxychloride was removed in vacuo. Distillation of the residue gave the title compound with boiling point 130° C./1 mm Hg.

EXAMPLE 14

Tetraethyl [2-(p-chlorophenoxy)-ethoxymethylene]-bisphosphonate

Anhydrous zinc chloride (10 g) was added at 150° C. to a mixture of dichloromethyl 2-(p-chlorophenoxy)-ethyl ether (5.1 g) and triethyl phosphite (6.9 ml). When the evolution of ethyl chloride ceased, the mixture was cooled, taken up in ether (250 ml), washed with aqueous sodium bicarbonate, dried and evaporated. Unreacted triethyl phosphite was removed in vacuo, and the crude product was used in the next step without further purification.

EXAMPLE 15

Disodium [2-(p-chlorophenoxy)-ethoxymethylene]-bisphosphonate

Tetraethyl [2-(p-chlorophenoxy)-ethoxymethylene]-bisphosphonate (5 g) was refluxed with concentrated hydrochloric acid (50 ml) for 3 hours. The hydrochloric acid was removed completely in vacuo, and the residue was taken up in ethanol. The disodium salt was precipitated by the addition of sodium 2-ethylhexanoate in ethanol and isolated by filtration in crystalline form.

NMR ((CD$_3$)$_2$SO/D$_2$O): $\delta$=3.7 (t, 1H), 4.0–4.2 (m, 4H), 6.95 (d, 2H), and 7.35 (d, 2H) ppm.

EXAMPLE 16

Disodium [2-(phenoxy)-ethoxymethylene]-bisphosphonate

This compound is prepared by substituting phenol for p-chlorophenol in Example 12 and following the procedures described in Examples 12–15.

EXAMPLE 17

Disodium [2-(phenylthio)-ethoxymethylene]-bisphosphonate

The title compound is prepared as described in Example 16 by substituting thiophenol for phenol.

EXAMPLE 18

(Phenoxymethylene)-bisphosphonic acid

A mixture of tetraethyl (phenoxymethylene)-bisphosphonate (20 g) and 6N hydrochloric acid (150 ml) was refluxed overnight and the resulting solution was evaporated to dryness in vacuo. Residual hydrochloric acid was removed by repeated evaporation with absolute ethanol. The residue was taken up in acetone (7 ml) and ether (200 ml) was added. The crystalline product was filtered, washed with ether and dried in vacuo.

M.p. 187°–188° C.

NMR ((CD$_3$)$_2$SO): $\delta$=4.66 (t, J=17 Hz, 1H) and 6.8–7.4 (m, 5H) ppm.

EXAMPLE 19

Disodium (phenoxymethylene)-bisphosphonate

A solution of (phenoxymethylene)-bisphosphonic acid (53 g) in water (300 ml) was titrated with 2N sodium hydroxide to pH=5.5. The title compound was precipitated by the addition of acetone (1500 ml). The crystalline salt was filtered and washed with acetone. Drying in vacuo over potassium hydroxide at room temperature gave the title compound in the form of a tetrahydrate.

Microanalysis: Calculated: C: 21.89, H: 4.20, H$_2$O: 18.7. Found: C: 21.80, H: 4.09, H$_2$O: 18.3.

Drying in vacuo at 60° C. gave a monohydrate.

Microanalysis: Calculated: C: 25.47, H: 3.05, H$_2$O: 5.4. Found: C: 25.54, H: 3.15, H$_2$O: 5.1.

EXAMPLE 20

By following the procedure described in Recueil Des Travaux Chimiques Des Pays-Bas 84, 1251 (1965), the following formates were prepared:

4-Chlorophenyl formate: B.P. 52° C./0.5 mmHg
4-Bromophenyl formate: B.p. 110° C./15 mmHg
4-Fluorophenyl formate: B.p. 70° C./15 mmHg
2,4-Dichlorophenyl formate: B.p. 60° C./0.1 mmHg 4-Tolyl formate: B.p. 80° C./15 mmHg
4-Tert-butylphenyl formate: B.p. 110° C./15 mmHg
1-Naphthyl formate: B.p. 100° C./0.4 mmHg
2-Naphthyl formate: B.p. 110° C./0.1 mmHg
4-Nitrophenyl formate: M.p. 71°-72° C.
4-Methoxyphenyl formate: B.p. 115° C./15 mmHg
3-(Trifluoromethyl)-phenyl formate: B.p. 70° C./15 mmHg

EXAMPLE 21

The following dichloromethyl ethers were prepared according to the procedure described in Recueil Des Travaux Chimiques Des Pays-Bas 90, 556–561 (1971):

Dichloromethyl 4-chlorophenyl ether: B.p. 68° C./0.2 mmHg
Dichloromethyl 4-bromophenyl ether: B.p. 135° C./15 mmHg
Dichloromethyl 4-fluorophenyl ether: B.p. 90° C./15 mmHg
Dichloromethyl 2,4-dichlorophenyl ether: B.p. 82° C./0.15 mmHg
Dichloromethyl 4-tolyl ether: B.p. 48° C./0.04 mmHg
Dichloromethyl 4-tert-butylphenyl ether: B.p. 140° C./15 mmHg
Dichloromethyl 1-naphthyl ether: B.p. 125° C./0.25 mmHg
Dichloromethyl 2-naphthyl ether: B.p. 130° C./0.35 mmHg
Dichloromethyl 4-nitrophenyl ether: B.p. 130° C./0.1 mmHg
Dichloromethyl 4-methoxyphenyl ether: B.p. 80° C./0.1 mmHg
Dichloromethyl 3-(trifluoromethyl)-phenyl ether: B.p. 90° C./15 mmHg

EXAMPLE 22

By following the procedure described in Example 8 and substituting the dichloromethyl ethers of Example 21 for dichloromethyl phenyl ether, the following compounds were prepared:

Tetraethyl (4-chlorophenoxymethylene)-bisphosphonate

NMR (CDCl$_3$): $\delta$ = 1.2–1.6 (m, 12H), 4.0–4.5 (m, 8H), 4.75 (t, J = 17 Hz, 1H) and 6.95–7.45 (m, 4H) ppm.

Tetraethyl (4-bromophenoxymethylene)-bisphosphonate

NMR (CDCl$_3$): $\delta$ = 1.31 (t, 6H), 1.33 (t, 6H), 4.20 (m, 8H), 4.77 (t, 1H), 7.00 (m, 2H), and 7.37 (m, 2H) ppm.

Tetraethyl (4-fluorophenoxymethylene)-bisphosphonate

NMR (CDCl$_3$): $\delta$ = 1.32 (t, 6H), 1.34 (t, 6H), 4.20 (m, 8H), 4.72 (t, 1H) and 7.00 (m, 4H) ppm.

Tetraethyl (2,4-dichlorophenoxymethylene)-bisphosphonate

NMR (CDCl$_3$): $\delta$ = 1.2–1.4 (m, 12H), 4.1–4.5 (m, 8H), 4.88 (t, J = 17 Hz, 1H) and 7.0–7.4 (m, 3H) ppm.

Tetraethyl (4-tolyloxymethylene)-bisphosphonate

NMR (CDCl$_3$): $\delta$ = 1.15–1.50 (m, 12H), 2.28 (s, 3H), 3.9–4.5 (m, 8H), 4.77 (t, J = 17 Hz, 1H) and 7.00 (m, 4H) ppm.

Tetraethyl (4-tert-butylphenoxymethylene)-bisphosphonate

NMR (CDCl$_3$): $\delta$ = 1.28 (s, 9H), 1.29 (m, 12H), 4.20 (m, 8H), 4.85 (t, 1H), 7.00 (m, 2H), and 7.30 (m, 2H) ppm.

Tetraethyl (1-naphthyloxymethylene)-bisphosphonate

NMR (CDCl$_3$): $\delta$ = 1.05–1.50 (m, 12H), 3.9–4.5 (m, 8H), 5.12 (t, J = 17 Hz, 1H), 7.0–8.0 (m, 6H), and 8.2–8.5 (m, 1H) ppm.

Tetraethyl (2-naphthyloxymethylene)-bisphosphonate

NMR (CDCl$_3$): $\delta$ = 1.2–1.4 (m, 12H), 4.0–4.5 (m, 8H), 5.04 (t, J = 17 Hz, 1H), 7.20–7.55 (m, 4H), and 7.60–7.85 (m, 3H) ppm.

Tetraethyl (4-nitrophenoxymethylene)-bisphosphonate

In this case the reaction mixture was stirred overnight at room temperature instead of 45° C.

NMR (CDCl$_3$): $\delta$ = 1.2–1.5 (m, 12H), 4.0–4.55 (m, 8H), 4.92 (t, J = 16 Hz, 1H), 7.18 (d, J = 9 Hz, 2H), and 8.22 (d, J = 9 Hz, 2H) ppm.

Tetraethyl (4-methoxyphenoxymethylene)-bisphosphonate

NMR (CDCl$_3$): $\delta$ = 1.31 (t, 6H), 1.34 (t, 6H), 3.76 (s, 3H), 4.20 (m, 8H), 4.71 (t, 1H), 6.80 (m, 2H), and 7.02 (m, 2H) ppm.

Tetraethyl (3-(trifluoromethyl)-phenoxymethylene)-bisphosphonate

NMR (CDCl$_3$): $\delta$ = 1.32 (t, 6H), 1.33 (t, 6H), 4.25 (m, 8H), 4.85 (t, 1H), and 7.33 (m, 4H) ppm.

EXAMPLE 23

(4-Tolyloxymethylene)-bisphosphonic acid

Tetraethyl (4-tolyloxymethylene)-bisphosphonate was hydrolyzed with 6N hydrochloric acid as described in Example 18. The crude acid crystallized from acetone-ether to yield a colourless crystalline compound with m.p. 186°–189° C.

NMR ((CD$_3$)$_2$SO): $\delta$ = 2.22 (s, 3H), 4.59 (t, J = 17 Hz, 1H), and 7.0 (m, 4H) ppm.

EXAMPLE 24

(2,4-Dichlorophenoxymethylene)-bisphosphonic acid

Trimethyl bromosilane (17.3 ml) was added to a stirred solution of tetraethyl (2,4-dichlorophenoxymethylene)-bisphosphonate (5.0 g) in methylene chloride (18 ml). After 3 hours at room temperature, the mixture was evaporated in vacuo, and residual trimethyl bromosilane was removed by repeated evaporation with methylene chloride. The residue was stirred overnight in ethanol and evaporated in vacuo. Crystallization from ether gave the title compound as colourless crystals.

NMR ((CD$_3$)$_2$SO): $\delta$ = 4.82 (t, J = 17 Hz, 1H), 7.3 (m, 2H), and 7.51 (bs, 1H) ppm.

EXAMPLE 25

(1-Naphthyloxymethylene)-bisphosphonic acid

This compound was prepared from tetraethyl (1-naphthyloxymethylene)-bisphosphonate according to the procedure described in Example 24. Colourless crystals with m.p. 244° C. (dec.).

NMR ((CD$_3$)$_2$SO): $\delta$ = 4.97 (t, J = 17 Hz, 1H), 7.0–7.6 (m, 5H), 7.8 (m, 1H), and 8.3 (m, 1H) ppm.

EXAMPLE 26

Disodium (2-naphthyloxymethylene)-bisphosphonate

By following the procedure described in Example 24 tetraethyl (2-naphthyloxymethylene)-bisphosphonate was transformed into the title compound in the form of the free acid which was dissolved in absolute ethanol and treated with an excess of benzylamine to form a crystalline tris-benzylamine salt. The free acid was liberated from the tris-benzylamine salt in water by treatment with an excess of Dowex 50 W (H+-form). The ion exchange resin was filtered, and the filtrate was titrated with 2N sodium hydroxide to pH=5.5. Concentration in vacuo and addition of acetone gave a colourless crystalline disodium salt with was isolated by filtration and dried in vacuo.

NMR (D$_2$O): δ=4.78 (t, J=16 Hz, 1H), 7.2–7.6 (m, 4H), and 7.7–7.9 (m, 3H) ppm. HDO=4.66 ppm was used as internal reference.

EXAMPLE 27

Tetraethyl (4-aminophenoxymethylene)-bisphosphonate

A solution of tetraethyl (4-nitrophenoxymethylene)-bisphosphonate (11 g) in methanol (120 ml) in a nitrogen atmosphere was cooled in ice and treated with hydrazine hydrate (5.3 ml) and 10% palladium on carbon (2.4 g). Stirring was continued for 3 hours at room temperature, and the catalyst was removed by filtration. The filtrate was evaporated in vacuo, and the crude product was purified by column chromatography on silica gel to give a colourless oil.

NMR (CDCl$_3$): δ=1.23–1.40 (m, 12H), 4.0–4.4 (m, 8H), 4.66 (t, J=17 Hz, 1H), 6.59 (d, J=9 Hz, 2H), and 6.94 (d, J=9 Hz, 2H) ppm.

EXAMPLE 28

(4-Aminophenoxymethylene)-bisphosphonic acid

This compound was prepared from tetraethyl (4-aminophenoxymethylene)-bisphosphonate by following the procedure of Example 18.

NMR (D$_2$O+NaOD): δ=4.17 (t, J=15 Hz, 1H), 6.61 (d, J=9 Hz, 2H), and 6.85 (d, J=9 Hz, 2H) ppm. HDO=4.66 ppm was used as internal reference.

EXAMPLE 29

3-(Phthalimido)-propyl formate

A mixture of 3-(phthalimido)-propanol (20.5 g) and formic acid (33 ml) was refluxed overnight and evaporated in vacuo to leave a yellow oil which crystallized from absolute ethanol to give colourless crystals with m.p. 68°–70° C.

EXAMPLE 30

Dichloromethyl 3-(phthalimido)-propyl ether

A mixture of 3-(phthalimido)-propyl formate (17 g), phosphorus pentachloride (15.2 g) and alcoholfree chloroform was heated for 1 hour on the steam bath. After cooling and addition of ether, the crystalline product was isolated by filtration. M.p. 101°–103° C.

EXAMPLE 31

Dichloromethyl 2-methoxyethyl ether

A mixture of formic acid (22.6 ml) and 2-methoxyethanol (23.8 ml) was refluxed overnight. After cooling, water and solid sodium bicarbonate in excess was added. The mixture was extracted twice with ether, and the organic phases were dried. Ether was removed by distillation at atmospheric pressure, and 2-methoxyethyl formate was then distilled in vacuo. B.p. 50° C./20 mmHg.

A mixture of 2-methoxyethyl formate (10.4 g) and phosphorus pentachloride (20.8 g) was stirred until a clear solution was formed. Fractionation in vacuo gave the title compound with b.p. 62° C./20 mmHg.

EXAMPLE 32

Dichloromethyl cyclohexyl ether

Cyclohexyl formate (12.8 g) and phosphorus pentachloride (20.8 g) were stirred until a clear solution was formed. Phosphorus oxychloride was removed in vacuo at room temperature, and the crude product was used in the next step without purification.

EXAMPLE 33

Dichloromethyl benzyl ether

This compound was prepared from benzyl formate and phosphorus pentachloride as described in Example 32.

EXAMPLE 34

Tetraethyl (2-methoxyethoxymethylene)-bisphosphonate

Diethyl phosphite (18.0 ml) was added dropwise at 20° C. to a stirred suspension of 55% sodium hydride (5.45 g) in dry tetrahydrofuran (100 ml). After stirring for a further 15 minutes, the mixture was cooled in ice, and dichloromethyl 2-methoxyethyl ether (7.15 g) was added during 15 minutes. The mixture was stirred at room temperature for 1 hour, diluted with saturated aqueous sodium chloride and extracted with chloroform. The organic phase was dried and evaporated to leave an oil which was purified by chromatography on silica gel. The pure title compound was isolated as a colourless oil.

NMR (CDCl$_3$): δ=1.25–1.43 (m, 12H), 3.36 (s, 3H), 3.6 (m, 2H), 3.9 (m, 2H), and 3.9–4.4 (m, 9H) ppm.

EXAMPLE 35

By following the procedure described in Example 34 and by substituting the dichloromethyl ethers of Examples 32, 33 and 30 for dichloromethyl 2-methoxyethyl ether, the following three compounds were prepared as colourless oils:

Tetraethyl (cyclohexyloxymethylene)-bisphosphonate

NMR (CDCl$_3$): δ=1.28–1.42 (m, 12H), 1.0–2.1 (m, 10H), 3.5–3.8 (m, 1H), 4.11 (t, J=17 Hz, 1H), and 4.1–4.4 (m, 8H) ppm.

Tetraethyl (benzyloxymethylene)-bisphosphonate

NMR (CDCl$_3$): δ=1.25–1.41 (m, 12H), 4.06 (t, J=17 Hz, 1H), 4.0–4.4 (m, 8H), 4.84 (s, 2H), and 7.35 (m, 5H) ppm.

Tetraethyl (3-(phthalimido)-propoxymethylene)-bisphosphonate

NMR (CDCl$_3$): δ=1.2–1.6 (m, 12H), 2.0 (m, 2H), 3.65–4.5 (m, 13H), and 7.6–7.9 (m, 4H) ppm.

EXAMPLE 36

(2-Methoxyethoxymethylene)-bisphosphonic acid, tris-benzylamine salt

A solution of tetraethyl (2-methoxyethoxymethylene)-bisphosphonate (4.0 g) in methylene chloride (16 ml) was cooled in ice and treated with trimethyl bromosilane (16.2 ml). The mixture was stirred at room temperature for 2 hours and evaporated in vacuo. The residue was stirred with absolute ethanol overnight at room temperature and evaporated in vacuo to leave the crude acid which was taken up in absolute ethanol (30 ml) and treated with benzylamine (4.5 ml). The colourless crystalline title compound was isolated by filtration.

NMR ($D_2O$): $\delta$=3.09 (s, 3H), 3.4–3.55 (m, 2H), 3.48 (t, J=15 Hz, 1H), 3.62–3.75 (m, 2H), 3.99 (s, 6H) and 7.30 (s, 15H) ppm. HDO=4.66 ppm was used as internal reference.

EXAMPLE 37

By following the procedure of Example 36 and by substituting tetraethyl (cyclohexyloxymethylene)-bisphosphonate or tetraethyl (benzyloxymethylene)-bisphosphonate for tetraethyl (2-methoxyethoxymethylene)-bisphosphonate, the following two compounds were prepared:

(Cyclohexyloxymethylene)-bisphosphonic acid, tris-benzylamine salt

NMR ($D_2O$): $\delta$=0.8–2.0 (m, 10H), 3.3–3.6 (m, 1H), 3.71 (t, J=16 Hz, 1H), 4.03 (s, 6H), and 7.3 (s, 15H) ppm. HDO=4.66 ppm was used as internal reference.

(Benzyloxymethylene)-bisphosphonic acid, tris-benzylamine salt

NMR ($D_2O$): $\delta$=3.72 (t, J=15 Hz, 1H), 4.71 (s, 2H), and 7.3 (s, 5H) ppm. HDO=4.66 ppm was used as internal reference.

EXAMPLE 38

(2-Hydroxyethoxymethylene)-bisphosphonic acid, tris-benzylamine salt

A mixture of tetraethyl (2-methoxyethoxymethylene)-bisphosphonate (2 g) and 6N hydrochloric acid (40 ml) was refluxed overnight and evaporated to dryness in vacuo. Traces of hydrochloric acid were removed by repeated evaporation with absolute ethanol. The crude product was dissolved in absolute ethanol, and benzylamine in excess was added. The crystalline salt was isolated by filtration and dried in vacuo.

NMR ($D_2O$): $\delta$=3.50 (t, J=16 Hz, 1H), 3.5–3.75 (m, 4H), 4.03 (s, 6H), and 7.33 (m, 15H) ppm. HDO=4.66 ppm was used as internal reference.

EXAMPLE 39

(3-Aminopropoxymethylene)-bisphosphonic acid

A mixture of tetraethyl (3-(phthalimido)-propoxymethylene)-bisphosphonate (4.4 g) and 6N hydrochloric acid (25 ml) was refluxed overnight. After cooling, the mixture was diluted with water and extracted twice with ether. The aqueous phase was evaporated to dryness, and the residue was stirred with absolute ethanol. The title compound was isolated by filtration and dried in vacuo.

NMR ($D_2O$+NaOD): $\delta$=1.65–2.0 (m, 2H), 3.09 (t, 2H), 3.55 (t, J=16 Hz, 1H) and 3.81 (t, 2H) ppm. HDO=4.66 ppm was used as internal reference.

EXAMPLE 40

Disodium (4-chlorophenoxymethylene)-bisphosphonate

This compound was prepared from tetraethyl (4-chlorophenoxymethylene)-bisphosphonate by following the procedure described in Example 26.

NMR($D_2O$): $\delta$=4.55 (t, J=16 Hz, 1H), 7.01 (d, J=9 Hz, 2H), and 7.26 (d, J=9 Hz, 2H) ppm. HDO=4.66 ppm was used as internal reference.

EXAMPLE 41

By following the procedure of Example 18, the following compounds were prepared:

(4-Bromophenoxymethylene)-bisphosphonic acid

NMR (($CD_3$)$_2$SO): $\delta$=4.66 (t, 1H), 7.00 (d, 2H), 7.40 (d, 2H), and 9.80 (s, 4H) ppm.

(4-Fluorophenoxymethylene)-bisphosphonic acid

NMR (($CD_3$)$_2$SO): $\delta$=4.59 (t, 1H), 7.05 (m, 4H), and 9.90 (s, 4H) ppm.

(3-Trifluoromethyl)-phenoxymethylene)-bisphosphonic acid

NMR (($CD_3$)$_2$SO): $\delta$=4.65 (t, 1H), 7.30 (m, 4H), and 9.60 (s, 4H) ppm.

(4-Nitrophenoxymethylene)-bisphosphonic acid

NMR ($CD_3OD$+DCl): $\delta$=5.13 (t, J=16 Hz, 1H), 7.31 (d, J=9 Hz, 2H), and 8.23 (d, J=9 Hz, 2H) ppm.

EXAMPLE 42

Disodium (4-tert-butylphenoxymethylene)-bisphosphonate

Tetraethyl (4-tert-butylphenoxymethylene)-bisphosphonate was transformed into the title compound as described in Example 26.

NMR ($D_2O$): $\delta$=1.23 (s, 9H), 4.57 (t, J=16 Hz, 1H), 7.04 (d, J=9 Hz, 2H), and 7.38 (d, J=9 Hz, 2H) ppm. HDO=4.66 ppm was used as internal reference.

EXAMPLE 43

(4-Methoxyphenoxymethylene)-bisphosphonic acid

Tetraethyl (4-methoxyphenoxymethylene)-bisphosphonate (4 g) was dissolved in trimethyl bromosilane (16.4 ml). After 3 hours at room temperature, the mixture was evaporated in vacuo. The remaining oil was heated with absolute ethanol (30 ml) on the steam bath for 2 hours. Evaporaton in vacuo and crystallization from ether gave the title compound as colourless crystals.

NMR (($CD_3$)$_2$SO): $\delta$=3.68 (t, 3H), 4.51 (t, 1H), 6.80 (d, 2H), 7.00 (d, 2H), and 9.10 (s, 4H) ppm.

EXAMPLE 44

(4-Hydroxyphenoxymethylene)-bisphosphonic acid

Tetraethyl (4-methoxyphenoxymethylene)-bisphosphonate (2 g) and concentrated hydrochloric acid (20 ml) were refluxed overnight. Evaporation to dryness in vacuo gave the title compound as an oil which crystallized.

NMR ((CD$_3$)$_2$SO): δ=4.40 (t, 1H), 6.6 (m, 2H), 6.9 (m, 2H), and 7.8 (m, 5H) ppm.

EXAMPLE 45

Tetraethyl (1-phenoxypropylidene)-bisphosphonate

Tetraethyl (phenoxymethylene)-bisphosphonate (1.14 g) was added to a suspension of 55% sodium hydride (0.15 g) in dimethylformamide (10 ml). After 45 minutes at room temperature, ethyl iodide (0.49 ml) was added, and the mixture was left overnight at room temperature, diluted with ethyl acetate and washed with 40% aqueous calcium chloride. The organic phase was dried and evaporated to leave an oil which was purified by chromatography on silica gel. The title compound was isolated as a colourless oil.

NMR (CDCl$_3$): δ=1.06 (t, 3H), 1.35 (t, 12H), 2.12 (m, 2H), 4.30 (m, 8H), and 7.0–7.4 (m, 5H) ppm.

EXAMPLE 46

By following the procedure of Example 45 and by substituting methyl iodide, butyl bromide or benzyl bromide, respectively, for ethyl iodide, the following compounds were prepared:

Tetraethyl (1-phenoxyethylidene)-bisphosphonate

NMR (CDCl$_3$)-δ=1.38 (t, 12H), 1.56 (t, 3H), 4.25 (m, 8H), and 7.0–7.4 m, 5H) ppm.

Tetraethyl (1-phenoxypentylidene)-bisphosphonate

NMR (CDCl$_3$): δ=0.75 (t, 3H), 1.0–1.5 (m, 4H), 1.34 (t, 6H), 1.36 (t, 6H), 2.0 (m, 2H), 4.25 (m, 8H), and 7.0–7.4 (m, 5H) ppm.

Tetraethyl (1-phenoxy-2-phenylethylidene)-bisphosphonate

Colourless crystalline compound with m.p.: 90°–92° C.

NMR (CDCl$_3$): δ=1.12 (t, 6H), 1.24 (t, 6H), 3.46 (t, 2H), 4.10 (m, 8H), and 7.0–7.5 (m, 10H) ppm.

EXAMPLE 47

Tetraethyl (1-n-butoxypentylidene)-bisphosphonate

Tetraethyl (n-butoxymethylene)-bisphosphonate (1.2 g) was added to a stirred solution of potassium tert-butoxide (0.37 g) in tert-butanol (5 ml). After 30 minutes at room temperature, butyl bromide (0.36 ml) was added, and the mixture was refluxed for 8 hours. After cooling, the mixture was diluted with ethyl acetate and washed with water. The organic phase was dried and evaporated to give an oil which was purified by chromatography to yield the title compound.

NMR (CDCl$_3$): δ=0.92 (t, 6H), 1.5 (m, 8H), 1.34 (t, 12H), 2.10 (m, 2H), 3.75 (t, 2H), and 4.20 (m, 8H) ppm.

EXAMPLE 48

By following the procedure described in Example 47, and substituting ethyl iodide, octyl bromide, benzyl chloride or 3-phenyl-propyl bromide, respectively, for butyl bromide, the following compounds were prepared:

Tetraethyl (1-n-butoxypropylidene)-bisphosphonate

NMR (CDCl$_3$): δ=0.92 (t, 3H), 1.09 (t, 3H), 1.2–1.6 (m, 4H), 1.33 (t, 12H), 2.15 (m, 2H), 3.75 (m, 2H), and 4.20 (m, 8H) ppm.

Tetraethyl (1-n-butoxynonylidene)-bisphosphonate

NMR (CDCl$_3$): δ=0.88 (t, 3H), 0.92 (t, 3H), 1.2–1.4 (m, 4H), 1.26 (bs, 12H), 1.34 (t, 12H), 2.0 (m, 2H), 3.75 (m, 2H), and 4.20 (m, 8H) ppm.

Tetraethyl (1-n-butoxy-2-phenylethylidene)-bisphosphonate

Tetraethyl (1-n-butoxy-4-phenylbutylidene)-bisphosphonate

EXAMPLE 49

(1-phenoxypropylidene)-bisphosphonic acid

A solution of tetraethyl (1-phenoxypropylidene)-bisphosphonate (2.1 g) in trimethyl bromosilane (8 ml) was kept at room temperature overnight, followed by evaporation in vacuo. The residue was stirred overnight in absolute ethanol. Evaporation in vacuo gave the desired compound.

NMR ((CD$_3$)$_2$SO): δ=0.92 (t, 3H), 2.00 (m, 2H), 7.0–7.4 (m, 5H), and 8.4 (s, 4H) ppm.

EXAMPLE 50

By following the procedure described in Example 49, and substituting the tetraethyl esters of Examples 46, 47, and 48 for tetraethyl (1-phenoxypropylidene)-bisphosphonate, the following compounds were prepared:

(1-Phenoxyethylidene)-bisphosphonic acid

NMR ((CD$_3$)$_2$SO): δ=1.37 (t, 3H), 7.0–7.4 (m, 5H) and 7.8 (s, 4H) ppm.

(1-Phenoxypentylidene)-bisphosphonic acid

NMR ((CD$_3$)$_2$SO): δ=0.66 (t, 3H), 0.8 (m, 2H), 1.35 (m, 2H), 1.90 (m, 2H), 6.9–7.4 (m, 5H), and 8.05 (s, 4H) ppm.

(1-Phenoxy-2-phenylethylidene)-bisphosphonic acid

NMR ((CD$_3$)$_2$SO): δ=3.14 (t, 2H), 7.0–7.5 (m, 10H), and 8.2 (s, 4H) ppm.

(1-n-Butoxypentylidene)-bisphosphonic acid

NMR ((CD$_3$)$_2$SO): δ=0.87 (t, 6H), 1.35 (m, 8H), 1.90 (m, 2H), 3.75 (m, 2H), and 7.30 (s, 4H) ppm.

(1-n-Butoxypropylidene)-bisphosphonic acid

NMR ((CD$_3$)$_2$SO): δ=0.87 (m, 3H), 0.99 (t, 3H), 1.1–1.6 (m, 4H), 2.0 (m, 2H), 3.77 (m, 2H), and 8.9 (s, 4H) ppm.

(1-n-Butoxynonylidene)-bisphosphonic acid

NMR ((CD$_3$)$_2$SO): δ=0.86 (m, 6H), 1.24 (bs, 12H), 1.1–2.1 (m, 6H), 3.73 (m, 2H), and 7.40 (bs, 4H) ppm.

(1-n-Butoxy-2-phenylethylidene)-bisphosphonic acid (1-n-Butoxy-4-phenylbutylidene)-bisphosphonic acid

EXAMPLE 51

Tetra-(pivaloyloxymethyl) (phenoxymethylene)-bisphosphonate

A solution of (phenoxymethylene)-bisphosphonic acid (8.04 g) in absolute ethanol (50 ml) was added to a stirred solution of silver trifluoroacetate (33.15 g) in absolute ethanol (200 ml). The mixture was cooled in ice and filtered. Drying in vacuo gave tetrasilver (phenoxymethylene)-bisphosphonate as a beige powder (17.9 g) which was suspended in acetonitrile (360 ml)

and treated with iodomethyl pivalate (31.1 g). After stirring for 30 minutes at room temperature, the mixture was filtered, and the filtrate was evaporated in vacuo to leave a crude oil which was purified by chromatography on silica gel to give the title compound as a colourless oil.

NMR (CDCl$_3$): $\delta$=1.16 (s, 18H), 1.19 (s, 18H), 5.01 (t, 1H), 5.75 (m, 8H), and 7.15 (m, 5H) ppm.

EXAMPLE 52

Tetra-(acetoxymethyl) (n-butoxymethylene)-bisphosphonate

This compound was prepared as described in Example 51 by substituting (n-butoxymethylene)-bisphosphonic acid for (phenoxymethylene)-bisphosphonic acid and by substituting iodomethyl acetate for iodomethyl pivalate.

NMR (CDCl$_3$): $\delta$=0.92 (m, 3H), 1.3–1.6 (m, 4H), 2.15 (s, 12H), 3.74 (bt, 2H), 4.10 (t, 1H), and 5.80 (m, 8H) ppm.

EXAMPLE 53–77

By starting from the appropriately substituted phenols and by following the procedures described in Examples 20, 21, 8, 18, 27, and 44, the compounds of formula V are prepared

TABLE II $$\begin{array}{c} \text{O} \quad\ \text{H} \quad\ \text{O} \\ \| \quad\quad\ \| \\ \text{HO}-\text{P}-\text{C}-\text{P}-\text{OH} \\ |\quad\ |\quad\ | \\ \text{OH}\ \text{O}\ \ \text{OH} \\ | \\ \text{R} \end{array} \qquad \text{V}$$

| Ex. | R |
|---|---|
| 53 | 2-chlorophenyl |
| 54 | 2-bromophenyl |
| 55 | 3-bromophenyl |
| 56 | 2-fluorophenyl |
| 57 | 3-fluorophenyl |
| 58 | 2-tolyl |
| 59 | 3-tolyl |
| 60 | 2-(trifluoromethyl)-phenyl |
| 61 | 4-(trifluoromethyl)-phenyl |
| 62 | 2-nitrophenyl |
| 63 | 3-nitrophenyl |
| 64 | 2-methoxyphenyl |
| 65 | 3-methoxyphenyl |
| 66 | 2,3-dimethylphenyl |
| 67 | 2,4-dimethylphenyl |
| 68 | 2,5-dimethylphenyl |
| 69 | 2,6-dimethylphenyl |
| 70 | 3,4-dimethylphenyl |
| 71 | 3,5-dimethylphenyl |
| 72 | 4-iodophenyl |
| 73 | 4-ethylphenyl |
| 74 | 2-aminophenyl |
| 75 | 3-aminophenyl |
| 76 | 2-hydroxyphenyl |
| 77 | 3-hydroxyphenyl |

EXAMPLE 78

For the preparation of tablets, the following composition was made:

| Disodium (phenoxymethylene)-bisphosphonate | 1000 g |
|---|---|
| Corn starch | 700 g |
| Hydroxypropylcellulose | 15 g |
| Sodium carboxymethyl starch | 65 g |
| Magnesium stearate | 20 g |

Disodium (phenoxymethylene)-bisphosphonate was mixed with corn starch and granulated with a 5% ethanolic solution of hydroxypropylcellulose. The granules were dried at 50° C., sifted through a 0.7 mm sieve, mixed with sodium carboxymethyl starch and magnesium stearate and pressed to 8 mm circular plane tablets, each weighing 180 mg.

EXAMPLE 79

For the preparation of a sterile solution for injection, the following composition was prepared:

| Disodium (phenoxymethylene)-bisphosphonate | 50 g |
|---|---|
| Sodium chloride | 60 g |
| Sodium acetate | 20 g |
| Acetic acid | q.s. |
| Water for injection | to 10.000 ml |

Disodium (phenoxymethylene)-bisphosphonate, sodium chloride and sodium acetate were dissolved in water for injection, and the pH was adjusted to 5.2 by the addition of acetic acid.

The solution was diluted to 10 liters with water for injection and sterile filtered through a 0.2 $\mu$m membrane filter. The solution was filled aseptically in ampoules, each containing 1 ml.

I claim:

1. A compound of formula I

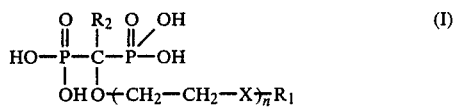

in which R$_1$ is a straight or branched, saturated or unsaturated aliphatic or alicyclic C$_1$-C$_{10}$ hydrocarbon radical, an aryl or an aryl-C$_1$-C$_4$-alkyl radical, R$_1$ if desired being unsubstituted or substituted with straight or branched C$_1$-C$_4$-alkyl, amino, C$_1$-C$_4$-alkylamino, di-(C$_1$-C$_4$-alkyl)-amino, carboxy, C$_1$-C$_4$-alkoxycarbonyl, hydroxy, C$_1$-C$_4$-alkoxy, phenoxy, mercapto, C$_1$-C$_4$-alkylthio, phenylthio, halogen, trifluoromethyl; R$_2$ stands for hydrogen, C$_1$-C$_8$-alkyl, aryl-C$_1$-C$_4$-alkyl or halogen; X is O or S, and n is an integer from 0 to 2; with the provisos that R$_2$ cannot be hydrogen or methyl if n=O and R$_1$ is methyl and that R$_2$ cannot be hydrogen or methyl if n=O and R$_1$ is unsubstituted n-butyl, n-pentyl or n-hexyl; and pharmaceutically acceptable, non-toxic salts and in the body easily hydrolyzable esters thereof.

2. A compound according to claim 1, in which R$_1$ stands for straight or branched C$_3$-C$_6$-alkyl, phenyl or benzyl optionally substituted with amino, hydroxy, methyl or halogen, and R$_2$ for hydrogen, straight or branched C$_1$-C$_4$ alkyl, benzyl or halogen; preferably R$_1$ being propyl, butyl, aminopropyl, aminobutyl, 2,2,2-trifluoroethyl, phenyl, or tolyl, and R$_2$ being hydrogen, methyl, ethyl or chlorine.

3. A mono-, di-, tri- or tetrabasic salt of a compound of formula I of claim 1, which is a salt selected from the group consisting of alkali metal salts, alkaline earth metal salts, salts with ammonia, lower alkylamines, lower alkanolamines, procaine, cycloalkylamines, benzylamines, and heterocyclic amines.

4. A mono-, di-, tri- or tetra ester of a compound of formula I of claim 1, which is an in vivo easily hydrolyzable ester, the ester forming residue being selected from the group consisting of alkanoyloxymethyl of three to six carbon atoms, 1-(alkanoyloxy)ethyl of four to seven carbon atoms, 1-methyl-1-(alkanoyloxy)ethyl of five to eight carbon atoms, alkoxycarbonyloxymethyl of three to six carbon atoms, 1-(alkoxycarbonyloxy)ethyl of four to seven carbon atoms, 1-methyl-1-(alkoxycarbonyloxy)ethyl of five to eight carbon atoms, 3-phthalidyl, 4-crotonolactonyl, γ-butyrolacton-4-yl, (2-oxo-1,3-dioxolen-4-yl)methyl, (5-methyl-2-oxo-1,3-dioxolen-4-yl)methyl, and (5-phenyl-2-oxo-1,3-dioxolen-4-yl)methyl as well as dialkylaminoalkyl, acetonyl, and methoxymethyl.

5. An ester according to claim 4, which is an alkanoyloxyalkyl or alkoxycarbonyloxy alkyl ester, in particular a pivaloyloxymethyl or ethoxycarbonyloxyethyl ester.

6. (Phenoxymethylene)-bisphosphonic acid and its salts and esters.

7. (2,2,2-Trifluoroethoxymethylene)-bisphosphonic acid and its salts and esters.

8. (4-Tolyloxymethylene)-bisphosphonic acid and its salts and esters.

9. (n-Propoxymethylene)-bisphosphonic acid and its salts and esters.

10. (4-Hydroxyphenoxymethylene)-bisphosphonic acid and its salts and esters.

* * * * *